(12) United States Patent
Traut et al.

(10) Patent No.: US 9,464,099 B2
(45) Date of Patent: Oct. 11, 2016

(54) METHOD FOR PRODUCING HYDROSILANES CONTAINING CARBON

(71) Applicants: Stephan Traut, Haltern am See (DE); Stephan Wieber, Karlsruhe (DE); Matthias Patz, Bottrop (DE); Michael Coelle, Schwanstetten (DE); Harald Stueger, Graz (AT); Christoph Walkner, Graz (AT)

(72) Inventors: Stephan Traut, Haltern am See (DE); Stephan Wieber, Karlsruhe (DE); Matthias Patz, Bottrop (DE); Michael Coelle, Schwanstetten (DE); Harald Stueger, Graz (AT); Christoph Walkner, Graz (AT)

(73) Assignee: EVONIK DEGUSSA GmbH, Essen (DE)

( * ) Notice: Subject to any disclaimer, the term of this patent is extended or adjusted under 35 U.S.C. 154(b) by 0 days.

(21) Appl. No.: 14/435,528

(22) PCT Filed: Oct. 31, 2013

(86) PCT No.: PCT/EP2013/072755
§ 371 (c)(1),
(2) Date: Apr. 14, 2015

(87) PCT Pub. No.: WO2014/082815
PCT Pub. Date: Jun. 5, 2014

(65) Prior Publication Data
US 2015/0329680 A1 Nov. 19, 2015

(30) Foreign Application Priority Data
Nov. 27, 2012 (DE) .......................... 10 2012 221 669

(51) Int. Cl.
*C07F 7/08* (2006.01)
*C08G 77/60* (2006.01)
*H01L 21/02* (2006.01)

(52) U.S. Cl.
CPC ........... *C07F 7/0821* (2013.01); *C07F 7/0827* (2013.01); *C07F 7/0896* (2013.01); *C08G 77/60* (2013.01); *H01L 21/02532* (2013.01); *H01L 21/02573* (2013.01); *H01L 21/02628* (2013.01)

(58) Field of Classification Search
None
See application file for complete search history.

(56) References Cited

U.S. PATENT DOCUMENTS

| 4,052,430 | A | * | 10/1977 | Yajima | C01B 31/36 528/31 |
| 5,596,117 | A | | 1/1997 | Itoh et al. | |
| 6,527,847 | B1 | * | 3/2003 | Matsuki | C09D 1/00 106/285 |
| 7,314,513 | B1 | * | 1/2008 | Zurcher | H01L 21/02532 106/287.14 |
| 7,422,708 | B2 | * | 9/2008 | Kunze | C09D 11/52 252/301.4 F |
| 7,674,926 | B1 | * | 3/2010 | Guo | C07F 9/5004 556/19 |
| 8,741,253 | B2 | | 6/2014 | Brausch et al. | |
| 8,889,092 | B2 | | 11/2014 | Wieber et al. | |
| 8,969,610 | B2 | | 3/2015 | Wieber et al. | |
| 2001/0021760 | A1 | * | 9/2001 | Matsuki | C07F 7/025 528/10 |
| 2009/0156775 | A1 | | 6/2009 | Sakamoto et al. | |
| 2012/0064302 | A1 | * | 3/2012 | Shimoda | B82Y 10/00 428/172 |
| 2012/0205654 | A1 | | 8/2012 | Stuetzel et al. | |
| 2012/0214005 | A1 | | 8/2012 | Wieber et al. | |
| 2012/0273805 | A1 | | 11/2012 | Wieber et al. | |
| 2013/0168824 | A1 | | 7/2013 | Wieber et al. | |
| 2013/0259790 | A1 | | 10/2013 | Wieber et al. | |
| 2013/0259791 | A1 | | 10/2013 | Brausch et al. | |

FOREIGN PATENT DOCUMENTS

| WO | 2012 038118 | 3/2012 |
| WO | 2014 202453 | 12/2014 |
| WO | 2014 202459 | 12/2014 |

OTHER PUBLICATIONS

"ROEMPP—Aluminiumchlorid—Georg Thieme Verlag KG", Retrieved from the internet: URL:https://roempp.thieme.de/roempp4.0/do/data/RD-01-01796, (Nov. 1, 2003), XP055098340, (Total pp. 2).
Koenig, B., et al., "Reduction Reactions Reduction of Carboxylic Acid Derivatives and Related Functionality", Retrieved from the internet: URL:http://www-oc.chemie.uni-regensburg.de/OCP/ch/chb/oc5/Reduction Reactions-08.pdf, (Mar. 27, 2008), XP055098342, (pp. 1-20).
Semenov, V.V., et al., "Graft Copolymers of Polyphenylsilane with Methyl Methacrylate", Polymer Science, Ser. A., vol. 37, No. 12, (1995), XP000551971, (pp. 1206-1211).
International Search Report Issued Jan. 31, 2014 in PCT/EP2013/072755 Filed Oct. 31, 2013.

* cited by examiner

*Primary Examiner* — Robert S Loewe
(74) *Attorney, Agent, or Firm* — Oblon, McClelland, Maier & Neustadt, L.L.P.

(57) ABSTRACT

The present invention provides processes for preparing carbon-containing hydridosilanes, in which an optionally boron- or phosphorus-doped hydridosilane is reacted without catalyst and reducing agent with at least one carbon source selected from linear, branched or cyclic carbosilanes, halogenated hydrocarbons, carbenes, alkyl azides, diazomethane, dimethyl sulphate or alcohols, the carbon-containing hydridosilane oligomers obtainable by the process and the use thereof.

13 Claims, No Drawings

METHOD FOR PRODUCING HYDROSILANES CONTAINING CARBON

The present invention relates to a process for preparing carbon-containing hydridosilanes, to the carbon-containing hydridosilanes themselves and to the use thereof.

Hydridosilanes and mixtures thereof are described in the literature as possible reactants for the production of silicon layers, which find use in the semiconductor industry inter alia. Hydridosilanes are understood to mean compounds which contain essentially only silicon and hydrogen atoms. Hydridosilanes may be gaseous, liquid or solid and are—in the case of solids—essentially soluble in solvents such as toluene or cyclohexane or in liquid silanes such as cyclopentasilane. Examples include monosilane, disilane, trisilane, cyclopentasilane and neopentasilane. Hydridosilanes having at least three or four silicon atoms may have a linear, branched or (optionally bi-/poly-)cyclic structure having Si—H bonds, and can be described by the respective generic formulae $Si_nH_{2n+2}$ (linear or branched; where n ≥2), $Si_nH_{2n}$ (cyclic; where n≥3) or $Si_nH_{2(n-i)}$ (bi- or polycyclic; n≥4; i={number of cycles}-1).

It is possible in principle to produce silicon layers via various processes. Among these, however, sputtering techniques have the disadvantage that they have to be performed under high vacuum. Gas phase deposition processes, for example CVD or PVD, have the further disadvantage that they require i) the use of very high temperatures in the case of a thermal reaction regime or ii) high energy densities in the case of introduction of the energy required for the decomposition of the precursor in the form of electromagnetic radiation. In both cases, it is possible only with a very high level of apparatus complexity to introduce the energy required to decompose the precursor in a controlled and homogeneous manner. Since the other processes for production of silicon layers are also disadvantageous, silicon layers are thus preferably formed via depositions from the liquid phase.

In such liquid phase processes for production of silicon layers, liquid reactants (optionally functioning as solvents for further additives and/or dopants) or liquid solutions containing the reactants (which are themselves liquid or solid) (and optionally further additives and/or dopants) are applied to the substrate to be coated and subsequently converted thermally and/or with electromagnetic radiation to a silicon layer. For example, US 2008/0022897 A1 discloses hydridosilane-containing coating compositions including dopants for production of thin semiconductor films.

Even though it is possible in principle to use many hydridosilanes for the silicon layer production, it has been found that only higher hydridosilanes, i.e. hydridosilanes having at least 10 silicon atoms, or solutions thereof give good coverage of the surface of customary substrates in the course of coating thereof and can lead to homogeneous layers with few defects. For this reason, processes for preparing higher hydridosilanes are of interest. Many higher hydridosilanes can be prepared by oligomerization of lower hydridosilanes. In the case of such an oligomerization of lower hydridosilanes viewed in a formal sense, one hydridosilane molecule of higher molecular weight is formed from two or more lower hydridosilane molecules after abstraction of hydrogen and/or relatively small hydridosilyl radicals.

However, silicon layers produced from pure hydridosilanes often still do not have satisfactory properties for semiconductor applications, especially for optoelectronic applications. Thus, it would be desirable to be able to produce silicon-based layers with greater optical bandgaps (which are suitable in principle to absorb radiation over a wide wavelength range in solar cells, i.e. constitute a "wide bandgap" material). It would also be desirable to produce silicon-based layers with a particularly small refractive index which enable better optical injection of the radiation. In addition, it would be desirable to be able to produce silicon-based layers with particularly good optical transmission.

U.S. Pat. No. 5,866,471 A discloses processes for producing thin semiconductor layers, in which not only solutions of hydridosilanes but also solutions comprising alkylated hydridosilanes are used. General processes for preparation of the alkylated hydridosilanes are not described. In the examples, a process for preparing alkylated hydridosilanes is disclosed, in which metallic sodium is used. However, this has the disadvantage that salts formed have to be removed in a costly and inconvenient manner, and disadvantageous metallated silane compounds can form as a by-product.

U.S. Pat. No. 6,020,447 A discloses a process for preparing alkylated hydridosilanes, in which a polysilane precursor is reacted with a reducing agent, preferably sodium, potassium, lithium and alloys thereof. Here too, disadvantageous ionic by-products are formed, and the reducing agent has to be removed in a costly and inconvenient manner.

U.S. Pat. No. 5,700,400 A discloses, in the context of a process for producing a semiconductive material, an intermediate of a dehydrogenating condensation of optionally alkylated mono-, di- or trisilane. However, the condensation is effected with addition of a catalyst selected from a metal or a metal compound of particular groups of the periodic table. These catalysts, however, have disadvantages. More particularly, it is disadvantageous that the removal thereof from the reaction mixture is very costly and inconvenient when particularly pure silicon layers are to be produced.

With respect to the outlined prior art, the problem addressed is thus that of providing a process for preparing carbon-containing hydridosilanes, which avoids the disadvantages of the prior art. More particularly, the problem addressed by the present invention is that of providing a process for preparing carbon-containing hydridosilanes, in which there is no need to remove reducing agents or catalysts in a costly and inconvenient manner, and in which no disadvantageous by-products form.

The problem which is thus addressed is solved in accordance with the invention by a process for preparing carbon-containing hydridosilanes, in which
an optionally boron- or phosphorus-doped hydridosilane is reacted
without catalyst and reducing agent
with at least one carbon source selected from
linear or branched carbosilanes of the generic formula $Si_bH_{2b+2-y}R_y$ where b ≥2, 1≤y≤2b+2 and R=—$C_1$-$C_{10}$-alkyl, —$C_6$-$C_{10}$-aryl,—$C_7$-$C_{14}$-aralkyl,
cyclic carbosilanes of the generic formula $Si_cH_{2c-y}R_y$ where c ≥3, 1y≤2c and R=—$C_2$-$C_{10}$-alkyl, —$C_6$-$C_{10}$-aryl, —$C_7$-$C_{14}$-aralkyl,
halogenated hydrocarbons of the generic formula $C_nH_{2n+2-y}X_y$ where 1≤n ≤5, 1≤y ≤12 and X=F, Cl, Br, I,
carbenes of the generic formula CRR' with R, R' =—H, —F, —Br, —I, —$C_1$-$C_{10}$-(cyclo)alkyl, —$C_2$-$C_{10}$-(cyclo)alkenyl, —$C_6$-$C_{10}$-aryl, —$C_1$-$C_{10}$-(cyclo)heteroalkyl, —$C_2$-$C_{10}$-heteroalkenyl, —$C_5$-$C_{10}$-heteroaryl, —$C_7$-$C_{14}$-aralkyl, —OR" where R''=—$C_1$-$C_{10}$-alkyl, —$C_2$-$C_{10}$-(cyclo)alkenyl, —$C_6$-$C_{10}$-aryl, —$NR'''_2$ where R'''=—$C_1$-$C_{10}$-alkyl, —$C_2$-$C_{10}$-(cyclo)alkenyl, —$C_6$-$C_{10}$-aryl, —$Si_n R^{IV}_{2n+1}$ where $R^{IV}$=—H, —$C_1$-$C_{10}$-(cyclo)alkyl, —$C_2$-$C_{10}$-(cyclo)alkenyl, —$C_6$-$C_{10}$-aryl, —(CO)-$R^V$ where $R^V$=—H, —$C_1$-$C_{10}$-(cyclo)alkyl, —$C_2$-$C_{10}$-(cyclo)alkenyl, —$C_6$-$C_{10}$-aryl, —(CO)—$OR^{vi}$ where $R^{vi}$=—H, —$C_1$-$C_{10}$-(cyclo)alkyl, —$C_2$-$C_{10}$-(cyclo)alkenyl, —$C_6$-$C_{10}$-aryl, —CN, —NC, —$SR^{vii}$ where $R^{vii}$=—H, —$C_1$-$C_{10}$-(cyclo)alkyl, —$C_2$-$C_{10}$-(cyclo)alkenyl, —$C_6$-$C_{10}$-aryl, —$S(O)_2 R^{viii}$ where $R^{viii}$=—H, —$C_1$-$C_{10}$-(cyclo)alkyl, —$C_2$-$C_{10}$-(cyclo)alkenyl, —$C_6 C_{10}$-aryl, —$P(R^{ix})_2$ where $R^{ix}$=—H, —$C_1$—$C_{10}$-(cyclo)alkyl, —$C_2$-$C_{10}$-(cyclo)alkenyl, —$C_6$-$C_{10}$-aryl, or where R and R' together represent a bidentate bridging radical selected from =$C_3$-$C_{20}$-(cyclo)alkyl, =$C_3$-$C_{20}$-(cyclo)alkenyl, =$C_3$-$C_{20}$-(cyclo)heteroalkyl, =$C_3$-$C_{20}$ heteroalkenyl and =$C_6$-$C_{14}$-(hetero)aralkyl, carbene analogues, especially CO and $CN^-$, alkyl azides of the generic formula $N_3 R^x$ where $R^x$=—$C_1$-$C_{10}$-(cyclo)alkyl, —$C_2$-$C_{10}$-(cyclo)alkenyl, —$C_6$-$C_{10}$-aryl, —$C_1$-$C_{10}$-(cyclo)heteroalkyl, —$C_2$-$C_{10}$-(cyclo)heteroalkenyl, —$C_5$-$C_{10}$-heteroaryl, —$C_7$-$C_{14}$-aralkyl, diazomethane $H_2 CN_2$, dimethyl sulphate $C_2 H_6 O_4 S$, or alcohols of the generic formula $HOR^{xi}$ where $R^{xi}$=—$C_1$-$C_{10}$-(cyclo)alkyl, —$C_2$-$C_{10}$-(cyclo)alkenyl, —$C_6$-$C_{10}$-aryl, —$C_1$-$C_{10}$-(cyclo)heteroalkyl, —$C_2$-$C_{10}$-(cyclo)heteroalkenyl, —$O_5$-$C_{10}$-heteroaryl, —$C_7$-$C_{14}$-aralkyl.

The hydridosilanes to be used as the reactant are compounds containing essentially only silicon and hydrogen atoms. They may include dopant atoms in a low proportion, especially boron or phosphorus. Hydridosilanes usable with preference satisfy the generic formula $Si_n \{BH\}_x \{PH\}_y H_{2n+2}$ where n=3-10, x=0 or 1 and y=0 or 1, with the proviso that at least one of the parameters x and y=0. These compounds are optionally boron- or phosphorus-doped hydridosilanes which may be linear or branched. Hydridosilanes of particularly good suitability are those of the generic formula $Si_n \{BH\}_x H_{2n+2}$ where n=3-10, x=0 or 1. The process according to the invention can be performed very particularly efficiently with hydridosilanes of the generic formula $Si_n H_{2n+2}$ where n=3-10. Corresponding compounds are linear or branched hydridosilanes. Very particular preference is given to the hydridosilanes $SiH(SiH_3)_3$, $Si(SiH_3)_4$ and $Si(SiH_3)_3 (SiH_2 SiH_3)$.

The oligomerization of the hydridosilanes in the presence of the carbon source forms carbon-containing hydridosilane oligomers of higher molecular weight compared to the hydridosilanes used. Because of the bonds which are broken and the subsequent recombination of the hydridosilanes used and optionally also of the carbon sources in the synthesis, these have a branched structure.

The process according to the invention additionally has the advantage that oligomers having a particularly homogeneous distribution of the carbon and silicon atoms, as a result of which these can also be used to produce silicon-containing layers with a particularly homogeneous distribution of these atoms. In addition, the process according to the invention has the advantage that even low carbon concentrations in the oligomer can be established efficiently.

The process according to the invention is performed without catalyst and reducing agent, meaning that it is performed without the presence of reducing agents (more particularly without the presence of elemental alkali metals or alkaline earth metals) and without the presence of compounds that would catalyse the oligomerization to give the carbon-containing hydridosilane (more particularly without the presence of transition metals, lanthanides, transition metal compounds or lanthanide compounds).

The process according to the invention is performed with at least one carbon source. Thus, the optionally boron- or phosphorus-doped hydridosilane can be reacted with one or more carbon sources. Preferably, because this leads to particularly good carbon-containing hydridosilanes, the process according to the invention is performed in such a way that the optionally boron- or phosphorus-doped hydridosilane is reacted with a carbon source. The carbon sources are selected from the following particular carbon sources elucidated in detail hereinafter: linear, branched and cyclic carbosilanes, halogenated hydrocarbons, carbenes, alkyl azides, alcohols, and the compounds diazomethane and dimethyl sulphate. How these compounds can be prepared is known to those skilled in the art.

The carbon sources used may be linear or branched carbosilanes of the generic formula $Si_b H_{2b+2-y} R_y$ where b ≥2, 1≤y≤2b+2 and R=$C_1$-$C_{10}$-alkyl, $C_6$-$C_{10}$-aryl, $C_7$-$C_{14}$-aralkyl, "$C_1$-$C_{10}$-Alkyl" radicals are understood here and hereinafter to mean radicals having 1 to 10 carbon atoms. Correspondingly, "$C_6$-$C_{10}$-aryl" radicals have 6 to 10 carbon atoms, and "$C_7$-$C_{14}$-aralkyl" radicals 7 to 14 carbon atoms. A prefix "$C_x$-$C_y$" here and hereinafter thus always denotes the minimum value x and the maximum value y for the carbons for the preferred radical designated more specifically thereafter. All alkyl radicals may be linear or else branched. In addition, all alkyl, aryl and aralkyl radicals may bear substituents. More particularly, all alkyl, aryl and aralkyl radicals may be halogenated. The linear or branched carbosilanes usable as the carbon source may have exclusively carbon-containing radicals (and thus be "pure" carbosilanes) or, in addition to these, may also have hydrogen atoms bonded directly to silicon (and thus be hydridocarbosilanes). Preference is given to linear or branched hydridocarbosilanes of the generic formula $Si_b H_{2b+2-y} R_y$ where b=2-20, y=1 to 2b+1 and R=$C_1$-$C_{10}$-alkyl, $C_6$-$C_{10}$-aryl, $C_7$-$C_{14}$-aralkyl, with which a higher reactivity arises compared to "pure" linear or branched carbosilanes, and with which, in addition, a more homogeneous distribution of the carbon in the oligomer can also be achieved.

The carbon sources used may also be cyclic carbosilanes of the generic formula $Si_c H_{2c-y} R_y$ where c≥3, 1≤y≤2c and R=$C_2$-$C_{10}$-alkyl, $C_6$-$C_{10}$-aryl, $C_7$-$C_{14}$-aralkyl. All alkyl radicals may be linear or else branched. In addition, all alkyl, aryl and aralkyl radicals may bear substituents. More particularly, all alkyl, aryl and aralkyl radicals may be halogenated. The cyclic carbosilanes usable as the carbon source may have exclusively carbon-containing radicals (and thus be "pure" carbosilanes) or, in addition to these, may also have hydrogen atoms bonded directly to silicon (and thus be hydridocarbosilanes). Preference is given to cyclic hydrogen-containing carbosilanes of the generic formula $Si_c H_{2c-y} R_y$ where c=3-20, y=1-(2c-1) and R=$C_2$-$C_{10}$-alkyl, $C_6$-$C_{10}$-aryl, $C_7$-$C_{14}$-aralkyl, with which a higher reactivity arises compared to "pure" cyclic carbosilanes and with which a more homogeneous distribution of the carbon in the oligomer can be achieved.

The carbon sources used may also be halogenated hydrocarbons of the generic formula $C_n H_{2n+2-y} X_y$ where 1≤n≤5, 1≤y≤12 and X=F, Cl, Br, I. Further preferably, halogenated compounds of the generic formula $CH_{4-y} X_y$ where X=F, Cl, Br, I and y=1-3 are used. Particular preference is given to using bromoform, dibromomethane, bromomethane, chloroform and dichloromethane.

The carbon sources used may also be carbenes of the generic formula CRR' where R, R'=—H, —F, —Br, —I, —$C_1$-$C_{10}$-(cyclo)alkyl, —$C_2$-$C_{10}$-(cyclo)alkenyl, —$C_6$-$C_{10}$-aryl, —$C_1$-$C_{10}$-(cyclo)heteroalkyl, —$C_2$-$C_{10}$-(cyclo)heteroalkenyl, —$C_5$-$C_{10}$-heteroaryl, —$C_7$-$C_{14}$-aralkyl, —OR" (where R"=—$C_1$-$C_{10}$-(cyclo)alkyl, —$C_2$-$C_{10}$-(cyclo)alkenyl, —$C_6$-$C_{10}$-aryl), —$NR'''_2$ (where R'''=—$C_1$-$C_{10}$-(cyclo)alkyl, —$C_2$-$C_{10}$-(cyclo)alkenyl, —$C_6$-$C_{10}$-aryl), —$Si_nR^{IV}_{2n+1}$ (where $R^{IV}$=—H, —$C_1$-$C_{10}$-(cyclo)alkyl, —$C_2$-$C_{10}$-(cyclo)alkenyl, —$C_6$-$C_{10}$-aryl), —(CO)—$R^v$ (where $R^v$=—H, —$C_1$-$C_{10}$-(cyclo)alkyl, —$C_2$-$C_{10}$-(cyclo)alkenyl, —$C_6$-$C_{10}$-aryl), —(CO)—$OR^{vi}$ (where $R^{vi}$=—H, —$C_1$-$C_{10}$-(cyclo)alkyl, —$C_2$-$C_{10}$-(cyclo)alkenyl, —$C_6$-$C_{10}$-aryl), —CN, —NC, —$SR^{vii}$ (where $R^{vii}$=—H, —$C_1$-$C_{10}$-(cyclo)alkyl, —$C_2$-$C_{10}$-(cyclo)alkenyl, —$C_6$-$C_{10}$-aryl), —$S(O)_2R^{viii}$ (where $R^{viii}$=—H, —$C_1$-$C_{10}$-(cyclo)alkyl, —$C_2$-$C_{10}$-(cyclo)alkenyl, —$C_6$-$C_{10}$-aryl), —$P(R^{ix})_2$ (where $R^{ix}$=—H, —$C_1$-$C_{10}$-(cyclo)alkyl, —$C_2$-$C_{10}$-(cyclo)alkenyl, —$C_6$-$C_{10}$-aryl). It is also possible to use carbenes of the generic formula CRR' in which R and R' together are a bidentate bridging radical selected from =$C_3$-$C_{20}$-(cyclo)alkyl, =$C_3$-$C_{20}$-(cyclo)alkenyl, =$C_3$-$C_{20}$-(cyclo)heteroalkyl, =$C_3$-$C_{20}$-(cyclo)heteroalkenyl or =$C_6$-$C_{14}$-(hetero)aralkyl. All alkyl, alkenyl, heteroalkyl and heteroalkenyl radicals may be linear or else branched. In addition, all alkyl, alkenyl, aryl, heteroalkyl, heteroalkenyl, heteroaryl and aralkyl radicals at individual, several or all positions (more particularly on carbon atoms and nitrogen atoms) may bear substituents. More particularly, individual, several or all of these positions may be halogenated or substituted by $C_3$-$C_6$-alkyl radicals. Particularly good results can be achieved with carbenes of the generic formula CRR' in which R and R'=—$C_4$-$C_{10}$-(cyclo)alkyl, —$C_4$-$C_{10}$-(cyclo)alkenyl, —$C_4$-$C_{10}$-aryl, -$C_4$-$C_{10}$-(cyclo)heteroalkyl, —$C_4$-$C_{10}$-heteroalkenyl, —$C_5$-$C_{10}$-heteroaryl, —$C_7$-$C_{14}$-aralkyl, or in which R and R' together are a bidentate bridging radical selected from =$C_4$-$C_{10}$-(cyclo)alkyl, =$C_4$-$C_{10}$-(cyclo)alkenyl, =$C_4$-$C_{10}$-(cyclo)heteroalkyl, =$C_4$-$C_{10}$-(cyclo)heteroalkenyl or =$C_6$-$C_{10}$-(hetero)aralkyl.

The carbon sources used may likewise be alkyl azides of the generic formula $N_3R^x$ where $R^x$=—$C_1$-$C_{10}$-(cyclo)alkyl, —$C_2$-$C_{10}$-(cyclo)alkenyl, —$C_6$-$C_{10}$-aryl, —$C_1$-$C_{10}$-(cyclo)heteroalkyl, —$C_2$-$C_{10}$-(cyclo)heteroalkenyl, —$C_5$-$C_{10}$-heteroaryl, -$C_7$-$C_{14}$-aralkyl, the compounds diazomethane $H_2CN_2$, dimethyl sulphate $C_2H_6O_4S$, and alcohols of the generic formula $HOR^{xi}$ where $R^{xi}$=—$C_1$-$C_{10}$-(cyclo)alkyl, —$C_2$-$C_{10}$-(cyclo)alkenyl, —$C_6$-$C_{10}$-aryl, —$C_1$-$C_{10}$-(cyclo)heteroalkyl, —$C_2$-$C_{10}$-(cyclo)heteroalkenyl, —$C_5$-$C_{10}$-heteroaryl, -$C_7$-$C_{14}$-aralkyl.

Advantages which can result for carbon sources mentioned over other carbon sources mentioned are that they lead particularly efficiently (i.e. particularly rapidly, in particularly high yield) to particularly homogeneous products. Some carbon sources may also be of particularly good suitability compared to other carbon sources from the same compound class for the reaction to be catalysed.

The process according to the invention can additionally be performed particularly efficiently when the hydridosilane has the generic formula $Si_nH_{2n+2}$ where n=3-10. Further preferably, the catalyst- and reducing agent-free reaction with the at least one carbon source is effected in the presence of at least one further hydridosilane compound having a weight-average molecular weight of at least 500 g/mol.

Particularly good boron- or phosphorus-doped hydridosilanes can be prepared from hydridosilanes of the generic formula $Si_nH_{2n+2}$ where n=3-10, a carbon source and at least one dopant selected from $AlMe_3$, $AlCl_3$, $BCl_3$, $BF_3$, diborane $(B_2H_6)$, $BH_3$:THF, $BEt_3$, $BMe_3$, $PH_3$ and $P_4$. Dopants usable with particular preference are $B_2H_6$, $BH_3$:THF and $P_4$, which lead to particularly good doping and which additionally have the advantage of increasing electrical dark conductivity. Because they are formed from three reactants, these oligomers are particularly homogeneous in relation to the distribution of the silicon, carbon and dopant atoms thereof, and as a result lead to particularly homogeneous layers with particularly good electrical properties.

The carbon source preferably has a weight-average molecular weight of 300 to 4000 g/mol (measured in cyclooctane against polybutadiene). These weight-average molecular weights of the carbon source particularly efficiently avoid unilateral silicon or carbon loss in the course of oligomerization and conversion.

The process according to the invention can likewise be performed in the presence of a Lewis acid. Preferably, however, no Lewis acid is present.

Preference is given to performing the conversion to the carbon-containing hydridosilane oligomer thermally and/or with electromagnetic radiation (especially IR, VIS or UV radiation). In the case of a thermal treatment, the reaction mixture is preferably heated to a temperature of 30 to 235° C. These temperatures can be established by means known to those skilled in the art. UV irradiation is additionally understood to mean irradiating with electromagnetic radiation having wavelengths of 120 to 380 nm. VIS radiation is understood to mean irradiating with electromagnetic radiation having wavelengths of 380 to 750 nm. IR irradiation, finally, is understood to mean irradiating with electromagnetic radiation having wavelengths of 750 nm to 1 mm. Corresponding radiation can be generated by means known to those skilled in the art. Preference is given to performing the conversion to the oligomer thermally or with UV radiation. Preferred reaction times are additionally between 0.1 and 12 h.

The reaction can be effected in the presence or absence of a solvent. Preference is given to performing the process according to the invention without solvent. If it is performed in the presence of a solvent, the preferred solvents used may be solvents selected from the group consisting of linear, branched or cyclic, saturated, unsaturated or aromatic hydrocarbons having one to 12 carbon atoms (optionally partially or fully halogenated), ethers, ketones and esters. Particular preference is given to n-pentane, n-hexane, n-heptane, n-octane, n-decane, dodecane, cyclohexane, cyclooctane, cyclodecane, dicyclopentane, benzene, toluene, m-xylene, p-xylene, mesitylene, tetrahydronaphthalene, decahydronaphthalene, diethyl ether, dipropyl ether, ethylene glycol dimethyl ether, ethylene glycol diethyl ether, ethylene glycol methyl ethyl ether, diethylene glycol dimethyl ether, diethylene glycol diethyl ether, diethylene glycol methyl ethyl ether, tetrahydrofuran, acetone, p-dioxane, acetonitrile, dimethylformamide, dimethyl sulphoxide, dichloromethane and chloroform. Solvents of particularly good usability are the hydrocarbons n-pentane, n-hexane, n-octane, n-decane, dodecane, cyclohexane, cyclooctane, cyclodecane, benzene, toluene, m-xylene, p-xylene, mesitylene. The solvent may account for 0.01 to 99% by weight of the total mass.

The present invention further provides the carbon-containing hydridosilane oligomer preparable by the process according to the invention.

The invention further provides for the use of the hydridosilane oligomers preparable by the process according to the invention for production of electronic or optoelectronic component layers, especially for photovoltaic applications or in transistors.

The invention likewise provides for the use of the hydridosilanes preparable by the process according to the invention for production of silicon-containing layers, preferably of elemental silicon layers.

The examples which follow are intended to provide further additional illustration of the subject-matter of the invention, without themselves having any limiting effect.

EXAMPLES

Synthesis of the higher carbon-containing poly-H-silanes
a) Neopentasilane (1.32 g) is mixed with methylisotetrasilane (1.18 g) and borane-THF complex (1.9 g; 1 M). The reaction solution is stirred at 50° C. for 4 h. GPC analysis shows a weight-average molecular weight of 500 g/mol.
b) Neopentasilane (3 g) is mixed with bromoform (3.48 ml) and $AlCl_3$ (0.145 g), and heated gradually to 100° C. In the course of this, a sudden onset of reaction with evolution of gas can be observed. After the reaction has abated, the solution is refluxed at 140° C. for a further 3 h.
c) Neopentasilane (1 g) is mixed with 1,3-diisopropylimidazolium-2-ylidenes (0.059 g) and borane-THF complex (1.46 g; 1 M) at room temperature. In the course of this, a sudden onset of reaction with evolution of gas can be observed. After the reaction has abated, the solution is coated according to Example 3.
d) Neopentasilane (1 g) is mixed with butanol (0.051 g) and borane-THF complex (1.46 g; 1 M). The reaction mixture is heated gradually to 140° C. and stirred at 140° C. for 3 h, in the course of which cloudiness of the solution can be observed.
e) Comparative synthesis: Neopentasilane (1 g) is mixed with borane-THF complex (1.46 g; 1 M) and stirred at 30° C. for 3 h. A GPC analysis shows a weight-average molecular weight of 580 g/mol.

Layer Production

Example 1

A glass substrate is coated at 6000 rpm with a formulation consisting of an oligomer from synthesis a) (0.15 g), cyclooctane (0.06 g) and toluene (0.54 g). The film is cured at 500° C. for 60 s. The layer thickness is 35 nm. The optical bandgap is 1.72 eV and the conductivity $1.52 \times 10^{-7}$ S/cm.

Example 2

A glass substrate is coated at 3000 rpm with a formulation consisting of an oligomer from synthesis b) (0.2 g), cyclooctane (0.06 g) and toluene (1.14 g). The film is cured at 500° C. for 60 s. The layer thickness is 205 nm. The optical bandgap is 2.42 eV and the electrical conductivity $2.1 \times 10^{-11}$ S/cm.

Example 3

A glass substrate is coated at 1000 rpm with a formulation consisting of an oligomer from synthesis c) (0.156 g), cyclooctane (0.016 g) and toluene (0.188 g). The film is cured at 500° C. for 60 s. The layer thickness is 101 nm. The optical bandgap is 1.74 eV and the electrical conductivity $2.1 \times 10^{-8}$ S/cm.

Example 4

A glass substrate is coated at 1000 rpm with a formulation consisting of an oligomer from synthesis d) (0.2 g), cyclooctane (0.039 g) and toluene (0.364 g). The film is cured at 500° C. for 60 s. The layer thickness is 144 nm. The optical bandgap is 1.64 eV and the electrical conductivity $3.2 \times 10^{-5}$ S/cm.

Comparative Example

A glass substrate is coated at 6000 rpm with a formulation consisting of an oligomer from the comparative synthesis (0.1 g), cyclooctane (0.1 g) and toluene (0.9 g). The film is cured at 500° C. for 60 s. The layer thickness is 98 nm. The optical bandgap is 1.54 eV.

The UV-VIS-NIR spectra were measured on the Varian Cary 5000 instrument. The carbon-containing silicon layers on glass (Corning Eagle XG) were measured in transmission between wavelength 200 nm and 1000 nm and plotted as a Tauc plot. The extrapolation of the linear region to the X axis gives the optical bandgap Eg.

The invention claimed is:
1. A process for preparing carbon-containing hydridosilanes, in which
an optionally boron- or phosphorus-doped hydridosilane is reacted
without catalyst and reducing agent
with at least one carbon source selected from
linear or branched carbosilanes of the generic formula $Si_bH_{2b+2-y}R_y$ where b≥2, 1≤y≤2b+2 and R=$C_1$-$C_{10}$-alkyl, $C_6$-$C_{10}$-aryl, $C_7$-$C_{14}$-aralkyl
cyclic carbosilanes of the generic formula $Si_cH_{2c-y}R_y$ where c≥3, 1≤y≤2c and R=$C_2$-$C_{10}$-alkyl, $C_6$-$C_{10}$-aryl, $C_7$-$C_{14}$-aralkyl,
halogenated hydrocarbons of the generic formula $C_nH_{2n+2-y}X_y$ where 1≤n≤5, 1≤y ≤12 and X=F, Cl, Br, I,
carbenes of the generic formula CRR' with R, R' =
—H, —F, —Br, —I, —$C_1$-$C_{10}$-(cyclo)alkyl, —$C_2$-$C_{10}$-(cyclo)alkenyl, —$C_6$-$C_{10}$-aryl,
—$C_1$-$C_{10}$-(cyclo)heteroalkyl, —$C_2$-$C_{10}$-(cyclo)heteroalkenyl, —$C_5$-$C_{10}$-heteroaryl,
—$C_7$-$C_{14}$-aralkyl,
—OR" where R" =—$C_1$-$C_{10}$-(cyclo)alkenyl, —$C_2$-$C_{10}$-(cyclo)alkenyl, —$C_6$-$C_{10}$-aryl,
—$NR'''_2$ where R'''=—$C_1$-$C_{10}$-(cyclo)alkenyl, —$C_2$-$C_{10}$-(cyclo)alkenyl, —$C_6$-$C_{10}$-aryl,
—$Si_nR^{IV}_{2n+1}$ where $R^{IV}$=—H, —$C_1$-$C_{10}$-(cyclo)alkyl, —$C_2$-$C_{10}$-(cyclo)alkenyl, —$C_6$-$C_{10}$-aryl,
—(CO)—$R^v$ where $R^v$=—H, —$C_1$-$C_{10}$-(cyclo)alkyl, —$C_2$-$C_{10}$-(cyclo)alkenyl, —$C_6$-$C_{10}$-aryl,
—(CO)—$OR^{vi}$ where $R^{vi}$ =—H, —$C_1$-$C_{10}$-(cyclo)alkyl, —$C_2$-$C_{10}$-(cyclo)alkenyl, —$C_6$-$C_{10}$-aryl,
—CN, —NC,
—$SR^{vii}$ where $R^{vii}$=—H, —$C_1$-$C_{10}$-(cyclo)alkyl, —$C_2$-$C_{10}$-(cyclo)alkenyl, —$C_6$-$C_{10}$-aryl,
—$S(O)_2R^{viii}$ where $R^{viii}$=—H, —$C_1$-$C_{10}$-(cyclo)alkyl, —$C_2$-$C_{10}$-(cyclo)alkenyl, —$C_6$-$C_{10}$-aryl,
—$P(R^{ix})_2$ where $R^{ix}$=—H, —$C_1$-$C_{10}$-(cyclo)alkyl, —$C_2$-$C_{10}$-(cyclo)alkenyl, —$C_6$-$C_{10}$-aryl,
or where R and R' together represent a bidentate bridging radical selected from =$C_3$-$C_{20}$-(cyclo)alkyl,

$=C_3-C_{20}$-(cyclo)alkenyl, $=C_3-C_{20}$-(cyclo)heteroalkyl, $=C_3-C_{20}$-(cyclo)heteroalkenyl or $=C_6-C_{14}$-(hetero)aralkyl,

—CO, CN⁻, alkyl azides of the generic formula $N_3R^x$ where $R^x=$ —$C_1-C_{10}$-(cyclo)alkyl, —$C_2-C_{10}$-(cyclo)alkenyl, —$C_6-C_{10}$-aryl, —$C_1-C_{10}$-(cyclo)heteroalkyl, —$C_2-C_{10}$-(cyclo)heteroalkenyl, $C_5-C_{10}$-heteroaryl, —$C_7-C_{14}$-aralkyl, diazomethane $H_2CN_2$, dimethyl sulphate $C_2H_6O_4S$, or alcohols of the generic formula $HOR^{xi}$, where $R^{xi}=$ —$C_1-C_{10}$-(cyclo)alkyl, —$C_2-C_{10}$(cyclo)alkenyl, —$C_6-C_{10}$-aryl, —$C_1-C_{10}$-(cyclo)heteroalkyl, —$C_2-C_{10}$(cyclo)heteroalkenyl, —$C_5-C_{10}$-heteroaryl, or —$C_7-C_{14}$-aralkyl.

2. The process according to claim 1, wherein the hydridosilane used as the reactant has the generic formula $Si_n\{BH\}_x\{PH\}_yH_{2n+2}$ where n=3–10, x=0 or 1 and y=0 or 1, with the proviso that at least one of the parameters x and y=0.

3. The process according to claim 2, wherein the hydridosilane used as the reactant has the generic formula $Si_nH_{2+l}$ where n=3–10.

4. The process according to claim 3, wherein the reaction with the at least one carbon source is effected in the presence of at least one further hydridosilane compound having a weight-average molecular weight of at least 500 g/mol.

5. The process according to claim 3, wherein the reaction of the hydridosilane with the carbon source is effected in the presence of at least one dopant selected from the group consisting of $AlMe_3$, $AlCl_3$, $BCl_3$, $BF_3$, $B_2H_6$, $BH_3$:THF, $BEt_3$, $BMe_3$, $PH_3$ and $P_4$.

6. The process according to claim 1, wherein the carbon source has a weight-average molecular weight of 300 to 4000 g/mol.

7. The process according to claim 1, wherein the reaction is effected thermally and/or with electromagnetic irradiation.

8. A carbon-containing hydridosilane oligomer preparable by a process according to claim 1.

9. A method for producing an electronic or optoelectronic component layer(s) comprising forming said layer(s) from a composition comprising a hydridosilane oligomer produced according to the process of claim 1.

10. A photovoltaic, transitor or other electronic or optoeltronic component layer(s) produced by the method according to claim 9.

11. A method for producing a silicon-containing layer(s) comprising forming layer(s) from a composition comprising a carbon-containing hydridosilane oligomer preparable according to claim 1.

12. Silicon-containing layer(s) produced by the method according to claim 11.

13. Elemental silicon-containing layer(s) produced by the according to claim 11.

\* \* \* \* \*

UNITED STATES PATENT AND TRADEMARK OFFICE
CERTIFICATE OF CORRECTION

PATENT NO. : 9,464,099 B2
APPLICATION NO. : 14/435528
DATED : October 11, 2016
INVENTOR(S) : Stephan Traut et al.

It is certified that error appears in the above-identified patent and that said Letters Patent is hereby corrected as shown below:

In the Claims

Column 10, Line 17, Claim 10, "transitor" should read --transistor--.

Signed and Sealed this
First Day of August, 2017

Joseph Matal
*Performing the Functions and Duties of the*
*Under Secretary of Commerce for Intellectual Property and*
*Director of the United States Patent and Trademark Office*